(12) United States Patent
Berg et al.

(10) Patent No.: US 11,523,936 B2
(45) Date of Patent: Dec. 13, 2022

(54) DEVICE AND METHOD FOR REDUCING THE BODY CORE TEMPERATURE OF A PATIENT FOR HYPOTHERMIA TREATMENT

(71) Applicant: BrainCool AB, Lund (SE)

(72) Inventors: Jon Berg, Dalby (SE); Christian Strand, Staffanstorp (SE); Martin Waleij, Lund (SE)

(73) Assignee: BrainCool AB, Lund (SE)

( * ) Notice: Subject to any disclaimer, the term of this patent is extended or adjusted under 35 U.S.C. 154(b) by 1429 days.

(21) Appl. No.: 15/519,051

(22) PCT Filed: Oct. 15, 2015

(86) PCT No.: PCT/EP2015/073918
§ 371 (c)(1),
(2) Date: Apr. 13, 2017

(87) PCT Pub. No.: WO2016/059173
PCT Pub. Date: Apr. 21, 2016

(65) Prior Publication Data
US 2017/0224528 A1   Aug. 10, 2017

(30) Foreign Application Priority Data

Oct. 15, 2014 (SE) .................................. 1451236-2
Oct. 15, 2014 (SE) .................................. 1451237-0

(51) Int. Cl.
*A61F 7/12* (2006.01)
*A61F 7/00* (2006.01)
*A61F 7/02* (2006.01)

(52) U.S. Cl.
CPC .............. *A61F 7/0053* (2013.01); *A61F 7/02* (2013.01); *A61F 2007/0002* (2013.01); *A61F 2007/0008* (2013.01); *A61F 2007/0011* (2013.01); *A61F 2007/0056* (2013.01); *A61F 2007/0086* (2013.01); *A61F 2007/0093* (2013.01); *A61F 2007/0096* (2013.01)

(58) Field of Classification Search
CPC .. A61F 7/0053; A61F 7/02; A61F 2007/0002; A61F 2007/0008; A61F 2007/0011; A61F 2007/0056; A61F 2007/0086; A61F 2007/0093; A61F 2007/0096; A61F 7/0097
See application file for complete search history.

(56) References Cited

U.S. PATENT DOCUMENTS 7,666,215 B2    2/2010  Callister et al.
2002/0128698 A1*  9/2002  Dobak, III ............. A61B 18/02
                                                      607/105
(Continued)

FOREIGN PATENT DOCUMENTS

WO      9944552 A1    9/1999
WO      0110323 A1    2/2001
(Continued)

*Primary Examiner* — Linda C Dvorak
*Assistant Examiner* — Yasamin Ekrami
(74) *Attorney, Agent, or Firm* — Capitol City TechLaw (57) ABSTRACT

A medical cooling device for reducing the body core temperature of a patient and a method for operating the same are provided. The cooling process provided by the medical cooling device is based on the state or degree of shivering of the patient.

20 Claims, 3 Drawing Sheets

(56) References Cited

U.S. PATENT DOCUMENTS

| | | |
|---|---|---|
| 2009/0131835 A1 | 5/2009 | Voorhees et al. |
| 2009/0312676 A1* | 12/2009 | Rousso .................... A61F 7/10 |
| | | 601/15 |
| 2010/0087900 A1* | 4/2010 | Flint ................... A61B 5/1101 |
| | | 607/104 |
| 2014/0222121 A1* | 8/2014 | Spence ................ A41D 13/005 |
| | | 607/104 |

FOREIGN PATENT DOCUMENTS

| | | |
|---|---|---|
| WO | 02055129 A2 | 7/2002 |
| WO | 2009065138 A1 | 5/2009 |
| WO | 2013013059 A1 | 1/2013 |

\* cited by examiner

DEVICE AND METHOD FOR REDUCING THE BODY CORE TEMPERATURE OF A PATIENT FOR HYPOTHERMIA TREATMENT

TECHNICAL FIELD

The present invention pertains to a medical cooling device and method for reducing the body core temperature of a patient by medically cooling of a body part of the patient, and in particular the brain of the patient, in a non-invasive manner.

CROSS-RELATED APPLICATIONS

This application claims priority under 35 USC 119(a)-(d) to SE patent application Nos. 1451237-0 and 1451236-2, both of which were filed on Oct. 15, 2014, the entire contents of both of which are incorporated herein by reference.

BACKGROUND

Medical cooling of parts of the human body for reducing the body core temperature for hypothermia treatment is a useful tool to reduce adverse impacts on the same under certain conditions. For example, medical cooling may be used for cooling the brain of patient suffering from a stroke. By reducing the temperature of the brain the risk of tissue damage is reduced for those parts of the brain lacking an adequate oxygen supply during the stroke. Another application of medical cooling is to cool the scalp for patients going through chemo therapy, to avoid undesirable hair loss.

In animal models of stroke, target temperatures of between 24° C. and 34° C. are most efficacious for reducing infarct size. However, even a brain temperature of 35° C. reduces the infarct volume by 30%. Cooling to levels of 32° to 34° C. generally requires sedation, mechanical ventilation and admission to an intensive care unit. Owing to the limited availability of intensive care beds in most countries, treatment of even a minority of acute stroke patients to those levels is therefore precluded by substantial practical and logistical problems. Temperature reductions to 35.5° C. or 35.0° C. have been shown to be feasible and safe in awake patients with acute ischemic stroke by surface cooling, in combination with for exapethidine to treat shivering. Some studies of patients with severe traumatic brain injuries indicate that temperatures of 35 to 35.5° C. seem to be the optimal temperature at which to treat patients with severe traumatic brain injuries.

Under normal conditions when the body temperature decreases beyond a certain point, e.g. around 35° C., the body starts to shiver in an attempt of regaining the heat loss. Depending on the person involuntary shivering may be initiated at different temperatures. Moreover, there are also pharmaceuticals that lower the onset temperature of involuntary shivering.

An improved medical cooling device of reducing the body core temperature would be advantageous.

SUMMARY

An object of the present invention is to eliminate or alleviate at least one of the drawbacks mentioned above, which is achieved by assigning to the device the characteristics according to claim 1.

According to a first aspect a control unit configured to control the operation of a medical cooling device conducting a non-invasive medical cooling process for reducing the body core temperature of a patient is provided. The operation of the medical cooling device is based on a number of process parameters. The control unit is configured to monitor at least one process parameter relating to a state of shivering of the patient. The control unit is further configured to make a decision relating to the state or degree of shivering of the patient based on the at least one monitored process parameter. The control unit is further configured to adapt a control process parameter based on the at least one monitored process parameter and the decision made to increase a body core temperature of the patient thereby putting the patient in a reduced state of shivering or a non-shivering state. Moreover, the control unit is configured to re-start the medical cooling process according to the adapted control process parameter.

According to a further aspect a medical cooling device for conducting a medical cooling process for cooling a body part of a patient is provided. The medical cooling device comprises a cooling fluid supply source, a supply line for supplying a flow of cooling fluid from the cooling fluid supply source to a patient, a return line for receiving the flow of cooling fluid from the patient, and the control unit of the first aspect.

In accordance with a further aspect, a method for controlling the operation of a medical cooling device conducting a medical cooling process for cooling a body part of a patient is provided. The operation of the medical cooling device is based on a number of process parameters, wherein the method comprises monitoring at least one process parameter relating to a state of shivering of the patient. The method further comprises making a decision relating to the state or degree of shivering of the patient based on the at least one monitored process parameter. Moreover, the method comprises adapting a control process parameter based on the at least one monitored process parameter and the decision made to put the patient in a reduced state of shivering or a non-shivering state. Furthermore, the method comprises re-starting the medical cooling process according to the adapted control process parameter.

The control unit, medical cooling device and method may be used to reduce the body core temperature of a patient during hypothermia treatment.

Control unit, medical cooling device, and method according to the aspects above are associated with a number of advantages. First and foremost, the negative impacts of the patient during medical cooling are avoided, by reducing or completely removing the waste of energy used by the patient in terms of shivering to counteract the medical cooling process. Another advantage is that the control unit, medical cooling device, and method may be used to detect a shivering state in any patient, irrespective of age, weight, and other factors having impact on the onset temperature of shivering.

BRIEF DESCRIPTION OF DRAWINGS

In order to explain the invention, a number of embodiments of the invention will be described below with reference to the drawings, in which.

DESCRIPTION OF EMBODIMENTS

An idea of the present invention is to consider the impact of shivering on the hypothermia treatment medical cooling process. In particular, an idea is to identify certain parameters relating to the state or degree of shivering of the patient during the medical cooling process. Based on the identified shivering state the medical cooling treatment process may be adapted such as to optimize the benefits to the patient and treatment result, and in this way the negative effects of the patient working against the cooling process is reduced. Hence, the aim of the adapted cooling treatment process is to maintain the body temperature of the patient just above the temperature at which shivering is detected.

The shivering activity of the patient, aiming at increasing the body temperature, opposes the purpose of the medical cooling process which is to cool the body part of the patient. The solution of the present invention takes this into account to optimize the medical cooling process.

By definition, shivering is involuntary, oscillatory muscular activity that can greatly increase one's metabolic heat production to counteract imminent hypothermia. Forceful shivering can increase heat production several fold. Shivering, in the absence of methods for measurement of brain temperature in usual care, is acting as a biological safeguard against temperatures below 35° C. At the same time, shivering may prevent the achievement of brain temperatures that are sufficiently low to obtain neuroprotection. However, there are pharmacological means of reducing the shivering threshold. For example, the combined administration of buspirone and dexmedetomidine has been shown to reduce the shivering threshold to 34° C.

Figure 1:
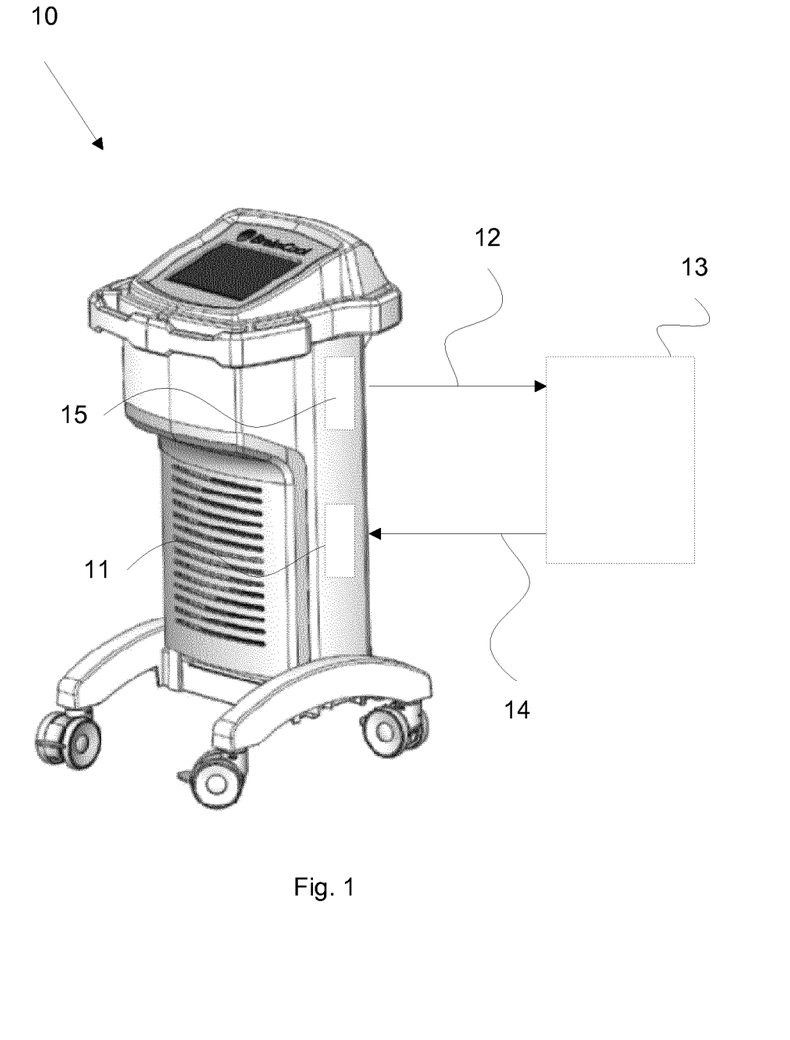
FIG. 1 is a schematic view of a medical cooling device according to one embodiment.

In an embodiment, according to FIG. 1, a medical cooling device 10 is provided. The medical cooling device 10 comprises a cooling fluid supply source 11 (schematically shown in FIG. 1 with dotted lines). The medical cooling device 10 comprises a supply line 12 for supplying a flow of cooling fluid from the cooling fluid supply source to a patient. A return line 14 is connected between the fluid distribution device 13 and the cooling fluid supply source. The supply line and the return line form part of a cooling circuit and may comprise tubes.

The cooling circuit may further comprise at least one cooling fluid distribution device 13, e.g. a wearable garment, which distributes the supplied cooling fluid around the body part of the body to be cooled. The at least one distribution device may contain a channel pattern for improving the cooling efficiency. The cooling fluid distribution device is connected at one end to the supply line 12 and at the other end to the return line 14. The cooling fluid distribution device 13 preferably has a shape being configured to encompass and tightly fit the body part of the patient to be cooled. The cooling of the body part of the patient is thus governed by means of conductive heat transfer between the cooling fluid in the distribution device 13 and the body part of the patient to the cooled. Hence, the cooling of the body part of the patient is preferably made ex vivo whereby there is no direct contact between the cooling fluid and the body part of the patient to be cooled.

The fluid distribution device 13 is non-invasive. Normally it is applied onto the patient's skin for cooling the body core temperature from outside of the body.

Ideally liquid cooling distribution device is preferably made of a material showing good heat conductive properties and comfortable fit in use. While metals have very good heat conductive properties, they are less suitable too allow for a comfortable fit on the body part. According to one embodiment, the at least one fluid distribution device is made of a silicon material which allows for a very comfortable fit however, having less heat conductive properties than a metal.

Depending on the type of material the temperature of the cooling fluid cooling supply source may be altered. For example, the temperature of the cooling fluid in the supply source when the distribution device is made of a silicon material may be between −9° C. and −6° C., such as −7° C. For a distribution device material having better (compared to silicon) heat conductive properties the temperature of the cooling fluid in the supply source may be higher than −6° C., such as −2° C., or even higher such as 4° C. to 5° C. Depending on the type of condition the patient is in, more than one distribution device may be connected to the medical cooling device. Each distribution device is supplied using a separate cooling circuit, i.e. a separate supply line and a separate return line.

It should be appreciated that the present invention is not limited to cooling fluid temperatures of −9 to −6° C. in the supply source. For some applications, e.g. where the cooling is continuously executed, the set fluid temperature in the cooling fluid supply source may be between +3 and +6° C., such as +4° C. A higher set fluid temperature in the cooling fluid supply source may alleviate the optional risk of frost damages during prolonged continuous cooling.

In an embodiment, one non-invasive distribution device 13 is arranged to be connected to the scalp of the patient, a further non-invasive distribution device 13 being arranged to be connected to the neck region of the patient, and yet a further non-invasive distribution device being arranged to be connected to one or several body parts having large muscle groups, such as the groin, or the groin in combination with the lower back and stomach muscles. Such a system will have three separate cooling circuits, each with an independent supply line and return line. Hence, the medical cooling device will have three separate outlets for connection to the separate supply lines and three separate inlets for connection to the separate return lines.

In an embodiment, the medical cooling device is semi-portable and contains a battery in order to allow the cooling system to run for 2-3 hours without access to a socket. This makes it possible to start the cooling in the emergency room (or already in the ambulance) and continue the cooling during the a couple of hours when a patient with for example stroke is moved around in the hospital before being placed in a bed in a hospital ward with access to a socket.

The cooling fluid supply source 11 may be integral with or connected to a refrigerator unit (not shown) for cooling the cooling fluid to a certain preset temperature.

The cooling fluid in the patient cooling circuit, i.e. flowing from the medical cooling device through the supply line, distribution device, return line and then back to the medical cooling device may be a conventional refrigerator liquid, such as a glycol based solution or optionally water. In the event the refrigerator unit utilizes a compressor for cooling the cooling fluid in the supply source, the compressor cooling circuit being separate from the patient cooling circuit may be using a conventional compressor refrigerant.

The medical cooling device 10 may further comprise a flow pump for providing flow rate of the cooling fluid in the cooling circuit according to the demand.

In an embodiment, the flow pump is a constant flow pump. Here the flow may be controlled using one or several flow control valves.

In one embodiment the flow control valve is of an ON/OFF type, e.g. solenoid being provided downstream the flow pump. In an ON position the flow of the cooling circuit allows for the rated flow of the flow pump is supplied to the supply line. In an OFF position no flow is supplied to the supply line whereby, the cooling fluid between the supply line and the return line is stationary. A mean flow is attained by using a precise timing schedule being stored in the control unit.

In an embodiment, the flow control valves may be proportional valves, which may be set to more than two positions for allowing different flow rates to pass depending on the position of the valve.

Two main factors affecting the cooling efficiency of the body part of the patient are the fluid flow rate and the temperature of the cooling fluid leaving the medical cooling device via the supply line 12. Increased flow for any cooling fluid temperature being below the temperature of the body part of the patient results in a higher rate of cooling. Similarly, for a constant flow rate any reduction in the cooling fluid temperature leaving the medical cooling device will result in a higher rate of cooling of the body part.

The medical cooling device 10 further comprises a control unit 15 (being schematically indicated with dotted lines in FIG. 1).

The control unit may be configured to allow for a precise flow in the supply line by means of controlling the flow control valves. For example, if the flow pump provides a rated flow of 6000 ml-8000/min, and the control unit is configured to provide a flow in the supply line of 2000 ml/min flow, the flow control valve needs to be in the OFF position during 20 seconds each minute. For example, the timing schedule may define the flow control valve to be OFF 10 times/minute with duration of 2 seconds each time. Alternatively, the flow control valve may be OFF 5 times/min with duration of 4 seconds each time in the OFF position. Alternatively, the control valve may be set to OFF once during 20 seconds per minute.

In an embodiment, the timing schedule of the ON/OFF valve(s) may be changed depending on the closeness to the expected onset of shivering state. For example, the ON/OFF valve(s) may be open until the cooling fluid is reduced to the demanded cooling fluid temperature, e.g. −7° C. and for a predetermined time after reaching the demanded cooling temperature, after which the flow is reduced by closing the ON/OFF valve(s) according a frequency/duration governed by the timing schedule. After another predetermined time period the closing frequency/duration may be altered further if desired.

Monitoring of the Process Parameters

The control unit is configured to monitor at least one process parameter relating to a state or degree of shivering of the patient. The control unit comprises a processor and a memory and is thus capable of computer processing capabilities.

Within the context of the present invention the at least one process parameter may relate to any one or combination of the following: the flow rate of the pump, the supply line fluid temperature, the return line fluid temperature, the temperature difference between the supply line fluid temperature and the return line fluid temperature, the instant and/or demanded cooling fluid temperature of the cooling fluid supply source, or the energy consumption of the cooling fluid supply source.

In practice the instant expression levels, e.g. in the form of magnitude or value, of the individual process parameters may be measured using at least one temperature sensor e.g. being provided connection to the supply line 12, the return line 14, and/or in or in the vicinity of the cooling fluid supply source.

A flow meter could be used to measure the cooling fluid flow rate in the supply line.

Alternatively, if on/off valves and a constant flow pump are used, a mean flow may be calculated based on the rated flow (e.g. 2l/min) of the pump and the time period during which the valve is in the on and off state, respectively. When the ON/OFF flow control valves using are set to OFF the cooling fluid may be stationary in the cooling circuit. This will mean that the temperature between the supply line and the return line will be heated by the distribution device by the body heat. Hence, in this case the control unit is configured to disregard temperature indications from the supply line temperature and return line temperature indicating an increase in return line temperature until the volume of cooling fluid being stationary in the supply line, distribution device, and the return line has been flushed out setting the ON/OFF valve to ON again.

The energy consumption could be measured e.g. by any conventional power consumption measuring device etc, such as an ammeter connected in series with the refrigerator unit.

In the normal case the medical cooling treatment may be started with a temperature of the cooling fluid in the cooling fluid supply source corresponding to the ambient temperature, e.g. being around 20° C. Hence, initially the supply source including the refrigerator unit, will require maximum power to cool the cooling fluid down to the set demand temperature of −9° C. to −6° C. During this time, the energy consumption will thus be high. Accordingly, the control unit may be configured to monitor the energy consumption of the refrigerator unit once the temperature of the cooling fluid supply source has reached the set demand temperature. Hence, when monitoring the energy consumption of the refrigerator unit the control unit also monitors the temperature in the supply liquid in order to make a decision of increased energy consumption due to onset of shivering.

In an embodiment, two temperature sensors are provided in the cooling fluid supply source.

Moreover, the control unit may be configured to store instant expression levels in its memory in order to derive rate of change, e.g. first derivative, and second derivative, based on at least two instant expression levels.

In an embodiment, the at least one process parameter relates to an instant temperature difference between the temperature of the cooling fluid exiting the medical cooling device 10 to the patient and the temperature of the cooling fluid returning to the medical cooling device 10 from the patient. An instant temperature difference being below a predetermined threshold may be considered being an indication of the patient being in a state of shivering.

In another embodiment, two or more successive instant temperature differences being below a predetermined threshold may be an indication of the patient being in a state of shivering.

In an embodiment, the at least one process parameter relates to a rate of temperature difference between the temperature of the cooling fluid exiting the medical cooling device 10 to the patient and the temperature of the cooling fluid returning to the medical cooling device 10 from the patient. Two or more successively monitored rates describing increasingly smaller temperature differences between the exiting cooling fluid and the returning cooling fluid may be considered being an indication that the patient is in a state of shivering.

In an embodiment, the at least one process parameter relates to the instant energy consumption of the medical cooling device being required to maintain a preset patient temperature, wherein an instant energy consumption increasing beyond a threshold is considered being an indication that the patient is in a state of shivering.

In an embodiment, the at least one process parameter relates to the rate of energy consumption of the medical cooling device being required to maintain a preset patient temperature. A rate of energy consumption increasing beyond a predetermined threshold is considered being an indication that the patient is in a state of shivering.

In an embodiment, the instant energy consumption or rate of energy consumption of the cooling fluid supply source is calculated using the following formula relating to the first law of thermodynamics:

$$Q(\text{energy}) = \dot{m} * CP * (T2 - T1),$$

wherein Q is the energy, ṁ is the mass flow of the cooling fluid in the supply line, CP represents a specific heat constant for the cooling fluid at constant pressure, T1 being the temperature of the exiting cooling fluid, and T2 being the temperature of the returning cooling fluid. Hence, instead of actively measuring the energy consumption of the cooling fluid supply source this can be calculated using the above formula.

In an embodiment, the at least one process parameter relates to the flow of cooling fluid exiting the medical cooling device.

Decision Process

The control unit is configured to make a decision relating to the state or degree of shivering of the patient based on the at least one monitored process parameter.

In an embodiment, when ON/OFF valves are used in the medical cooling device, the control unit is configured only to make a decision about shivering when there is a flow in the supply line. Hence, when the flow control valve(s) is set to OFF no decision about shivering will be made.

In order for a decision to be made the control unit may be configured to compare the instant expression level, e.g. magnitude or value, of the at least one monitored process parameter to a reference for said process parameter. The reference may relate to an expected expression level of the monitored process parameter. Alternatively, the reference may relate to a preset expression level threshold of the process parameter.

Alternatively or in combination with comparing instant expression levels, the control unit is capable of comparing expression level rates, e.g. the first or second derivative of the instant expression levels, of the monitored process parameter with a reference in form of an expression level reference rate. For example, a sudden accelerated increase of the energy consumption of the refrigerator unit may be a strong indication of the onset of shivering. Another significant indication of shivering is in the event that the return temperature starts to increase or in other words that the difference between the return line temperature T2 and the supply line temperature T1 starts to increase.

In order to utilize an expression level reference rate as reference the control unit is configured to derive a rate of the expression level based on at least two succeeding instant expression levels.

In an embodiment, as long as at least one comparison between either an expression level and reference expression level or a comparison between an expression level rate and an expression level reference rate indicates a state of shivering, the control unit is configured to make a decision that the patient is in a state of shivering.

In another embodiment, at least two comparisons in view of expression levels or expression level rates, both indicating a state of shivering, are required for the control unit to make a decision that the patient is in a state of shivering.

Example 1

In the table below one example of information relevant for the control unit to make a positive decision that the patient is in a state of shivering is shown. For simplicity, the example only refers to one cooling circuit comprising only one distribution device. However, more than one cooling circuits and/or more than one distribution device is also possible within the scope defined herein. In this example, the fluid temperature in the fluid supply source is set to −7° C.

| Time [minutes] | Tank temp (T1) [° C.] | Return flow temp (T2) [° C.] | Flow (ṁ) [kg/s] | Constant (Cp) [J/kgK] | Power consumption [W] | Power consumption (Exluding losses) [W] | Core Temp. [° C.] | Shivering |
|---|---|---|---|---|---|---|---|---|
| 0 | −7 | −4.8 | 0.033 | 4180 | 303 | 101 | 37 | NO |
| 20 | −7 | −4.5 | 0.031 | 4180 | 324 | 108 | 36.7 | NO |
| 40 | −7 | −4.6 | 0.032 | 4180 | 321 | 107 | 36.4 | NO |
| 60 | −7 | −4.5 | 0.033 | 4180 | 345 | 115 | 36.1 | NO |
| 80 | −7 | −4.7 | 0.031 | 4180 | 298 | 99 | 35.8 | NO |
| 100 | −7 | −4.9 | 0.033 | 4180 | 290 | 97 | 35.5 | NO |
| 120 | −7 | −1 | 0.031 | 4180 | 777 | 259 | 35.5 | YES |
| 140 | −7 | −1 | 0.032 | 4180 | 803 | 268 | 35.5 | YES |
| 160 | −7 | −2 | 0.015 | 4180 | 314 | 105 | 35.5 | NO |
| 180 | −7 | −1 | 0.012 | 4180 | 301 | 100 | 35.5 | NO |
| 200 | −7 | −1 | 0.011 | 4180 | 276 | 92 | 35.5 | NO |
| 220 | −7 | −1 | 0.013 | 4180 | 326 | 109 | 35.5 | NO |
| 240 | −7 | −1 | 0.011 | 4180 | 276 | 92 | 35.5 | NO |

As may be seen in the table during the first 100 minutes no indication of shivering is noticeable. After 100 minutes of cooling treatment the core temperature of the patient has been reduced from 37° C. to 35.5° C., and the return flow temperature lies steady at around −4.9° C. After 120 minutes from the start of treatment the situation has changed. Now the return temperature has increased to −1° C., which results in a significant increase in power consumption. Based on this information the control unit is arranged to decide that the patient is in a state of shivering. In this example the shivering state remains after 140 minutes. The second indication of shivering after 140 minutes from the start of treatment also verifies that the first indication of shivering was correct. Based on the positive shivering decision the control unit is configured to reduces the flow from 0.031 to 0.015 kg/s in the cooling circuit. After 160 minutes from the start of treatment there is no further shivering indication as the power consumption has returned to a non-shivering level. The return temperature is relatively constant between −2 to −1° C. throughout the cooling treatment, whereas the flow rate remains between 0.011 and 0.015 kg/s, since the power consumption remains at a non-shivering level. This means that the patient is put in a reduced state of shivering or a non-shivering state, thereby avoiding unnecessary waste of energy by the patient during the cooling treatment.

Example 2

Figure 3:
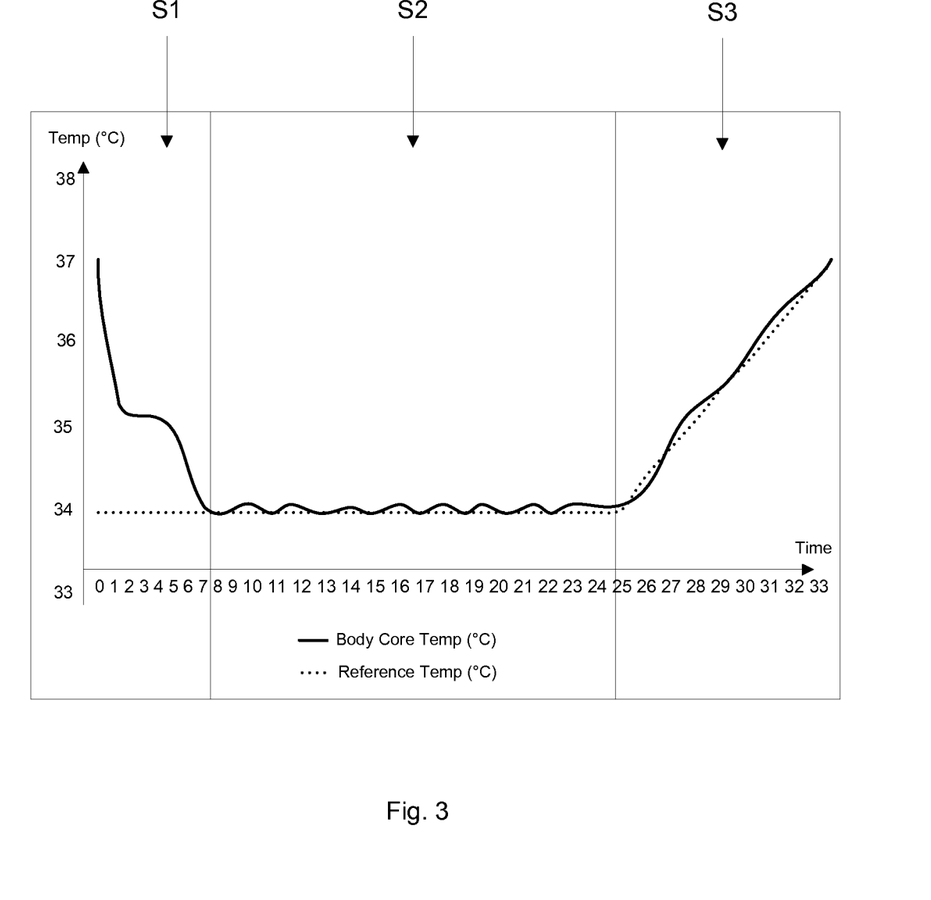
FIG. 3 illustrates a general body core temperature appearance of a patient subject to a medical cooling device not considering shivering.

Shivering may be detected based on monitoring different control process parameters depending on the stage of the cooling process. As shown in FIG. 3, a cooling process may be divided into three main stages; a first stage S1 during which the body temperature is decreased from normal down to a certain lowered body temperature, a second stage S2 during which the body temperature is maintained at the certain lowered core body temperature, and a third stage or rewarming stage S3 during which the body temperature is increased from the certain lowered body temperature back to the normal body temperature. The solid body core temperature curve shown in FIG. 3 generally represents the appearance for a common hypothermia treatment cooling process. A reference curve, indicated by a dotted line, is used as the target temperature for the medical cooling device. In a commonly known system the medical cooling device will work to reduce the temperature to the reference temperature regardless of any encountered shivering, as that shown by the flattened body core temperature curve just above 35 degrees between time 1 and 3 during the first stage S1.

As mentioned the first stage may pertain to the phase in which the cooling process is started until the body temperature has been cooled down to a certain level. In the first stage the monitored control process parameter may be the body temperature over time. The decision relating to the state or degree of shivering in the first stage may be taken based on a comparison between the body temperature curve representing the body temperature over time and an expected reference curve. In particular the derivates of said two curves may be compared. In the event the derivate of the body temperature curve differs to a certain extent from the derivate of the expected reference curve a state of shivering has been detected. In this way a state of shivering may be detected since the body temperature decrease rate tends to reduce when shivering is first encountered.

When the state of shivering has been decided upon, a second stage of the cooling process is initiated. During the second stage of the cooling process the body temperature is maintained close to the shivering temperature. During this stage, the state or degree of shivering may be decided upon by calculating the energy drawn from the patient. In other words, during the second stage, the control unit may monitor the energy consumption of the cooling fluid supply source or rate thereof in order to detect a state or degree of shivering. When the energy consumption is increased this is an indication of a state of shivering, since the more the cooling fluid supply source needs to cool the liquid to counteract the shivering increasing the body temperature. Hence, in the second stage it may not be necessary to monitor the body temperature since the body temperature per se does not add anything about the state of shivering.

Similarly to the first stage shivering may be detected during the third stage, i.e. the rewarming stage, by monitoring the body temperature curve and comparing it to an expected reference curve. Accordingly, a state of shivering may be detected in the third stage since the body temperature increase rate tends to increase when shivering is encountered.

Adapting Control Process Parameters

Based on the decision that the patient is in a state of shivering, the control unit 15 is configured to adapt at least one control process parameter and re-starting the medical cooling process according to the adapted control process parameter(s) thereby reducing the degree of shivering of the patient or completely avoiding the state of shivering.

A key aspect of reducing the degree of shivering or complete avoidance of shivering is to increase the body temperature to a level where little or no shivering may be detected. This may be achieved by adapting one or several control process parameters.

Normal practice for a hypothermia cooling device is to immediately increase the cooling power if the patient suffers from shivering, as shown in FIG. 3. The present invention does the opposite, since when shivering is detected the system allows the body core temperature of the patient to increase, e.g. by 0.5° C. in one hour. This minimizes the pain associated with shivering for the patient.

The control process parameter may relate to any one or combination of the following:

the flow rate of the pump,
the demanded cooling fluid temperature of the cooling fluid supply source,
a limitation of the electrical power submitted to the cooling fluid supply source, operation state and timing of flow control valves allowing or limiting the cooling fluid flow to the supply line.

In an embodiment, the control process parameter may be adapted according to any one of the following:

flow rate of the cooling fluid is decreased (e.g. by demanding the pump to decrease the flow rate);
temperature of the cooling fluid exiting the medical cooling device is increased;
electrical power to the refrigerator of the medical cooling device is reduced or restricted.

When the flow is controlled using a constant flow pump and one or more ON/OFF valves, the control unit may be configured adapt the operation state of the one or more ON/OFF valves, such as to change the flow in the cooling circuit. The control unit may additionally be configured to adapt the timing schedule, such as to extend the duration of the OFF state compared to a predetermined time period.

The temperature of the cooling fluid exiting the medical cooling device may be adapted by the control unit by setting a new higher control demand temperature to the refrigerator unit. The refrigerator unit then heats the cooling fluid according to the new control demand temperature of the supply source.

Alarm Signal

In an embodiment, the control unit 15 is further configured to activate an alarm signal in response to the decision made in that the patient is in a state of shivering. The alarm signal may trigger an aural, tactile and/or visual alarm in the medical cooling device. For example, a visual alarm may be presented on a display device of the medical cooling device. An aural alarm signal may be submitted via optional speakers provided on the medical cooling device. The control unit may be configured to provide an alarm signal in accordance with the guidance for alarm systems in medical electrical equipment and medical electrical systems (e.g. IEC standard IEC 60601-1-8)

Alternatively, or in combination the control unit may be configured to transmit the alarm signal to an external device, e.g. mobile terminal, to remotely indicate to the healthcare personnel that the patient is in a state of shivering.

Figure 2:
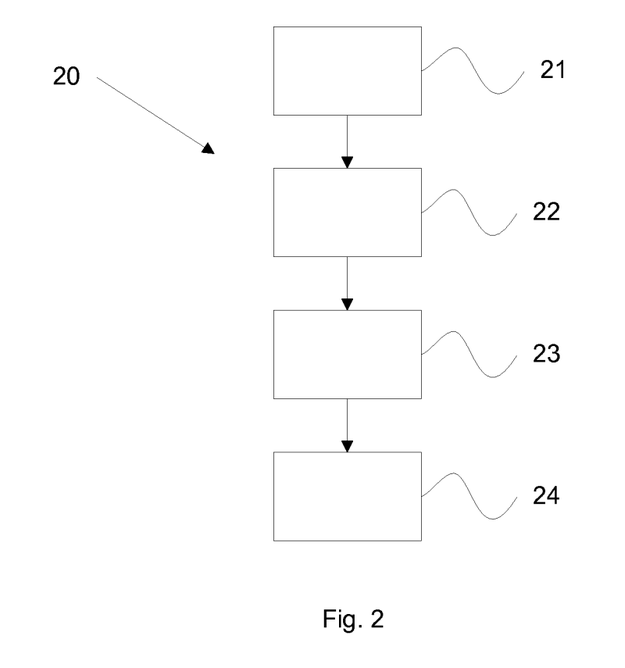
FIG. 2 illustrates a method according to an embodiment.

In an embodiment, according to FIG. 2, a method for controlling the operation of a medical cooling device 10 conducting a medical cooling process for cooling a body part of a patient is provided. The operation of the medical cooling device 10 is based on a number of process parameters. The method comprises the steps of:

monitoring 21 at least one process parameter relating to a state of shivering of the patient;

making 22 a decision relating to the state or degree of shivering of the patient based on the at least one monitored process parameter, adapting 23 a control process parameter based on the at least one monitored process parameter and the decision made; and re-starting 24 the medical cooling process according to the adapted control process parameter.

Applicability

One body part of particular interest is the scalp of the patient, and here the distribution device may be shaped like a cap or helmet. Scalp cooling particularly advantageous for lowering the brain temperature in patients suffering of acute stroke as well as patients undergoing chemo therapy to reduce hair loss.

However, cooling of the brain may also be advantageous after cardiac arrest, in neonatal hypoxia ischemia, insomnia or traumatic brain injury.

It should be appreciated that the medical cooling device, control unit, and method according to the embodiments presented herein may be used in combination with other methods for brain cooling such as infusion of cold saline or pharmacological cooling with antipyretics such as paracetamol. In the case of ischemic stroke, the medical cooling device, control unit, and method according to the embodiments presented herein may also be used in conjunction with reestablishment of cerebral perfusion.

Hypothermia with lowered brain temperature has been shown to be a robust neuroprotectant against a variety of brain injuries. Recently, a randomized crossover study showed that cooling of the frontal lobes with a scalp cooling device significantly reduced insomnia.

In usual care, the optimal target brain temperature seems to be 35.0°-35.5° C. Such low temperatures in the deep brain tissue cannot be reached with scalp cooling only. However, by adding cooling of the neck over the carotid arteries it is possible to reach the optimal brain temperature. The distribution device according to some embodiments may comprise such additional cooling of the neck over the carotid arteries.

In an embodiment, in addition to the scalp silicon cap, a separate neck band with temperature sensors is provided. The neck band is cooled by liquid coolant from the same cooling fluid supply source as the cap.

Brain cooling has been shown to be safe at least as long as the brain temperature stays at 34° C. or above.

The duration of brain cooling treatment may be anything from 30 minutes up to 24 hours or more. For stroke applications, treatment duration of up to at least 72 hours appears to provide advantageous results. However, some suggestions have been made to provide cooling treatment for up to 11 to 14 days or more depending on the type of condition of the patient.

Although some of the embodiments above have been described in relation to a stroke application, in which cooling of the brain is advantageous. It should be noted that the embodiments of the present invention is equally useful in the case of cardiac arrest. For patient suffering from a sudden cardiac arrest, body temperature control and cooling treatment to cause hypothermia can be a life saving intervention. This means that the body temperature of the patient is lowered to reduce the tissue damage due to lack of oxygen. Patients suffering from a cardiac arrest who receive a cooling treatment have a greater rate of survival and also have less risk of permanent injury, e.g. brain damage. Cooling treatment at cardiac arrest also protects all of the body organs, which each has different sensitivity for ischemia. For example, muscle tissue may cope with ichemia for hours whereas the brain may suffer great damage within only a couple of minutes. During cooling treatment of patients suffering from cardiac arrest it may be advantageous to reduce the body temperature to lower temperatures. According to an embodiment, the distribution device(s) may be provided one or more garments, each connected to one or more cooling circuits. In the case of cardiac arrest a larger part of the body, may be cooled down, and hence the distribution devices may cover a larger portion of the body, such as the legs, stomache area, arms, scalp and neck. In an embodiment, such a garment may be provided with a opening at the position of the heart such as to facilitate optional heart surgery, while keeping the garment on.

The invention claimed is:

1. A control unit configured to control the operation of a medical cooling device conducting a non-invasive medical cooling process for reducing the body core temperature of a patient, wherein the operation of the medical cooling device is based on a number of process parameters, the control unit being configured to:
monitor at least one process parameter relating to a state of shivering of the patient;
make a decision relating to the state or degree of shivering of the patient based on the at least one monitored process parameter;
adapt a control process parameter based on the at least one monitored process parameter and a decision made to increase a body core temperature of the patient thereby putting the patient in a reduced state of shivering or a non-shivering state; and
re-start the medical cooling process according to the adapted control process parameter;
wherein the at least one process parameter relates to a temperature difference between the temperature of a cooling fluid exiting the medical cooling device to the patient and the temperature of the cooling fluid returning to the medical cooling device from the patient.

2. The control unit according to claim 1, wherein the at least one process parameter relates to an instant energy consumption of the medical cooling device being required to maintain a preset patient temperature.

3. The control unit according to claim 1, wherein the control unit is configured to monitor the at least one process parameter by measuring an instant expression level of the at least one process parameter.

4. The control unit according to claim 3, further configured to derive a rate of change based on at least two instant expression levels.

5. The control unit according to claim 1, wherein a decision that the patient is in a state of shivering is made based on at least one correlation between an instant expression level of the at least one process parameter and a reference expression level.

6. The control unit according to claim 1, wherein a decision that the patient is in a state of shivering is made based on at least two successive correlations between two successive instant expression levels of the at least one process parameter and a reference expression level.

7. The control unit according to claim 1, wherein a decision that the patient is in a state of shivering is made based on at least one correlation between an expression level rate of the at least one process parameter and an expression level reference rate.

8. The control unit according to claim 7, wherein a decision that the patient is in a state of shivering is made based on at least two successive correlations between two successive expression level rates of the at least one process parameter and the expression level reference rate.

9. The control unit according to claim 1, wherein the temperature difference being below a temperature difference reference expression level is an indication of the patient being in a state of shivering.

10. The control unit according to claim 1, wherein two successive temperature differences being below a temperature difference reference expression level is an indication of the patient being in a state of shivering.

11. The control unit according to claim 2, wherein an increased rate of energy consumption of the medical cooling device being above a reference expression level is an indication of the patient being in a state of shivering.

12. The control unit according to claim 2, wherein the instant energy consumption is calculated using the following formula:

$$Q(\text{energy}) = \dot{m} * CP * (T2 - T1),$$

wherein Q is the energy, $\dot{m}$ is the mass flow of a cooling fluid in a supply line, CP represents a constant for the cooling fluid related to the specific heat at constant pressure, T1 being the temperature of the cooling fluid exiting the medical cooling device, and T2 being the temperature of the cooling fluid returning to the medical cooling device.

13. The control unit according to claim 1, wherein the control process parameter is selected from the group comprising: a flow rate of a cooling fluid, a temperature of the cooling fluid exiting the medical cooling device, an electrical power to a refrigerator unit of the medical cooling device, or an operation state and timing schedule of a flow control valve allowing or limiting the cooling fluid flow to a supply line.

14. The control unit according to claim 13, wherein based upon a decision made, by the control unit, that the patient is in a state of shivering the control process parameter is adapted according to any one of the following:
the flow rate of the cooling fluid is decreased;
the temperature of the cooling fluid exiting the medical cooling device is increased;
the electrical power to the refrigerator unit of the medical cooling device is reduced or restricted; or
setting the flow control valve to an OFF position for a predetermined time period or an extended time period in view of the predetermined time period.

15. The control unit according to claim 1, being further configured to activate an alarm signal in response to a decision made that the patient is in a state of shivering.

16. The control unit according to claim 1, further configured to select the at least one process parameter monitored depending on the current stage of the cooling process.

17. The control unit according to claim 1, wherein the at least one process parameter monitored in a first stage of the cooling process is different from the at least one process parameter monitored in a second stage of the cooling process.

18. A medical cooling device for conducting a non-invasive medical cooling process for reducing the body core temperature of a patient by cooling a body part of the patient, the medical cooling device comprising:
a cooling fluid supply source;
a supply line for supplying a flow of cooling fluid from the cooling fluid supply source to the patient;
a return line for receiving the flow of cooling fluid from the patient; and
a control unit configured to
monitor at least one process parameter relating to a state of shivering of the patient,
make a decision relating to the state or degree of shivering of the patient based on the at least one monitored process parameter,
adapt a control process parameter based on the at least one monitored process parameter and a decision made to increase a body core temperature of the patient thereby putting the patient in a reduced state of shivering or a non-shivering state, and
re-start the medical cooling process according to the adapted control process parameter;
wherein the at least one process parameter relates to a temperature difference between the temperature of a cooling fluid exiting the medical cooling device to the patient and the temperature of the cooling fluid returning to the medical cooling device from the patient.

19. The medical cooling device according to claim 18, further comprising:
a cooling fluid distribution device being connected at one end to the supply line and at the other end to the return line;
wherein the fluid distribution device has a shape configured to encompass the body part of the patient to be cooled;
wherein the cooling of the body part of the patient is governed by conductive heat transfer between the cooling fluid in the distribution device and the body part of the patient to the cooled.

20. A method for controlling the operation of a medical cooling device conducting a non-invasive medical cooling process for reducing the body core temperature of a patient by cooling a body part of a patient, wherein the operation of the medical cooling device is based on a number of process parameters, the method comprising:
monitoring at least one process parameter relating to a state of shivering of the patient;
making a decision relating to the state or degree of shivering of the patient based on the at least one monitored process parameter;
adapting a control process parameter based on the at least one monitored process parameter and a decision made to increase a body core temperature of the patient thereby putting the patient in a reduced state of shivering or a non-shivering state; and
re-starting the medical cooling process according to the adapted control process parameter;
wherein the at least one process parameter relates to a temperature difference between the temperature of a cooling fluid exiting the medical cooling device to the patient and the temperature of the cooling fluid returning to the medical cooling device from the patient.

\* \* \* \* \*